(12) United States Patent
Li et al.

(10) Patent No.: US 11,717,427 B2
(45) Date of Patent: Aug. 8, 2023

(54) CONVEYOR FOR IMPLANT HAVING AT LEAST ONE CAVITY

(71) Applicant: Shenzhen Lifetech Respiration Scientific Co., Ltd., Shenzhen (CN)

(72) Inventors: Shujun Li, Shenzhen (CN); Siyi Li, Shenzhen (CN); Anning Li, Shenzhen (CN)

(73) Assignee: Shenzhen Lifetech Respiration Scientific Co., Ltd., Shenzhen (CN)

( * ) Notice: Subject to any disclaimer, the term of this patent is extended or adjusted under 35 U.S.C. 154(b) by 428 days.

(21) Appl. No.: 16/771,902

(22) PCT Filed: Dec. 18, 2018

(86) PCT No.: PCT/CN2018/121713
§ 371 (c)(1),
(2) Date: Jun. 11, 2020

(87) PCT Pub. No.: WO2019/128771
PCT Pub. Date: Jul. 4, 2019

(65) Prior Publication Data
US 2021/0068998 A1    Mar. 11, 2021

(30) Foreign Application Priority Data
Dec. 28, 2017    (CN) .......................... 201711466871.2

(51) Int. Cl.
*A61F 2/95*    (2013.01)
*A61B 17/12*    (2006.01)
(Continued)

(52) U.S. Cl.
CPC ...... *A61F 2/9517* (2020.05); *A61B 17/00234* (2013.01); *A61B 17/12145* (2013.01);
(Continued)

(58) Field of Classification Search
CPC .............. A61F 2/9517; A61F 2002/043; A61F 2002/9511; A61B 17/00234;
(Continued)

(56) References Cited

U.S. PATENT DOCUMENTS 10,687,821 B2 * 6/2020 Li ........................ A61B 90/39
2006/0116709 A1    6/2006 Sepetka et al.
(Continued)

FOREIGN PATENT DOCUMENTS

| CN | 102209570 A | 10/2011 |
|---|---|---|
| CN | 202010169 U | 10/2011 |

(Continued)

OTHER PUBLICATIONS

Extended European Search Report dated Sep. 3, 2021, in corresponding European Application No. 18896625.3; 9 pages.
(Continued)

*Primary Examiner* — Diane D Yabut
*Assistant Examiner* — Rachel S Highland
(74) *Attorney, Agent, or Firm* — Maier & Maier, PLLC

(57) ABSTRACT

A conveyor for an implant having at least one cavity, including a conveying handle, a conveying cable, and a core wire. The conveying cable is a tubular body, a proximal end of the core wire is connected to the conveying handle, and a distal end of the core wire penetrates a distal end of the conveying cable from a proximal end of the conveying cable; a first control is provided on the conveying handle, and when the implant is connected to the distal end of the conveying cable, the first control controls the distal end of the core wire to extend into the implant to straighten the curved implant, or the first control controls the core wire to withdraw from the implant to restore the implant to a preset shape. The conveyor can load and release the implant on the conveyor, and be used in the entire implanting process.

11 Claims, 9 Drawing Sheets

(51) Int. Cl.
*A61B 17/00* (2006.01)
*A61B 1/018* (2006.01)
*A61B 1/267* (2006.01)
*A61F 2/04* (2013.01)

(52) U.S. Cl.
CPC ............. *A61B 1/018* (2013.01); *A61B 1/2676* (2013.01); *A61B 2017/00323* (2013.01); *A61B 2017/00367* (2013.01); *A61B 2017/00592* (2013.01); *A61B 2017/12054* (2013.01); *A61F 2002/043* (2013.01); *A61F 2002/9511* (2013.01)

(58) Field of Classification Search
CPC . A61B 17/12145; A61B 1/018; A61B 1/2676; A61B 2017/00323; A61B 2017/00367; A61B 2017/00592; A61B 2017/12054; A61B 2017/00809; A61B 2017/00867; A61B 2017/1205; A61B 17/12104; A61B 17/0057; A61B 2017/00623; A61B 2017/00632
See application file for complete search history.

(56) References Cited

U.S. PATENT DOCUMENTS

| | | | | |
|---|---|---|---|---|
| 2006/0276827 | A1* | 12/2006 | Mitelberg | A61B 17/12022 606/200 |
| 2007/0112409 | A1* | 5/2007 | Wu | A61F 2/95 606/108 |
| 2010/0094393 | A1 | 4/2010 | Cordeiro et al. | |
| 2010/0185233 | A1* | 7/2010 | Thommen | A61B 17/0057 606/213 |
| 2012/0310239 | A1 | 12/2012 | Stewart et al. | |
| 2015/0223955 | A1* | 8/2015 | Li | A61F 2/2436 606/108 |
| 2016/0317274 | A1* | 11/2016 | Liu | A61B 17/12122 |
| 2017/0156904 | A1* | 6/2017 | Liu | A61F 2/86 |
| 2018/0333157 | A1* | 11/2018 | Li | A61B 90/39 |

FOREIGN PATENT DOCUMENTS

| | | |
|---|---|---|
| CN | 102370533 A | 3/2012 |
| CN | 103655004 A | 3/2014 |
| CN | 103860299 A | 6/2014 |
| CN | 105455930 A | 4/2016 |
| CN | 106691626 A | 5/2017 |
| EP | 1782759 A2 | 5/2007 |
| EP | 3090692 A1 | 11/2016 |
| JP | 2016512118 A | 4/2016 |
| WO | 2015188705 A1 | 12/2015 |
| WO | 2016044188 A1 | 3/2016 |
| WO | 2016075544 A3 | 5/2016 |
| WO | 2016130536 A1 | 8/2016 |
| WO | 2017084347 A1 | 5/2017 |

OTHER PUBLICATIONS

Notification to Grant Patent Right for Invention dated Apr. 2, 2021, in connection with corresponding Chinese Application No. 201711466871.2 (3 pp., including machine-generated English translation).

Chinese Office Action dated Nov. 4, 2020, in connection with corresponding CN Application No. 201711466871.2 (12 pp., including machine-generated English translation).

English translation of International Preliminary Report on Patentability dated Jun. 30, 2020, in connection with corresponding International Application No. PCT/CN2018/121713; 4 pages.

Indian Examination Report dated Jul. 2, 2021, in connection with corresponding IN Application No. 202017024653; 5 pages.

International Search Report dated Mar. 15, 2019 and Written Opinion in corresponding International application No. PCT/CN2018/121713; 13 pages.

* cited by examiner

CONVEYOR FOR IMPLANT HAVING AT LEAST ONE CAVITY

FIELD

The embodiments relate to the field of interventional medicine, and in particular to a conveyor for an implant having at least one cavity.

BACKGROUND

Emphysema is a common disease, especially in the elderly with a higher incidence rate. Statistically, the survival rate of patients with end-stage emphysema after 5 years of disease is less than 50%. Traditionally, the medical treatment of emphysema includes oxygen inhalation, prevention of pulmonary infection, bronchospasmolysis and the like, but the curative effect is quite limited. Surgical treatment is mainly based on lung volume reduction surgery by delivering a lung volume reduction implant to a target region of the lungs of a human or animal body by means of a conveyor and releasing it, thereby compressing lung tissue and further reducing lung volume.

Since the implant is curled and has certain elasticity in a natural state, each curled part of the implant can be constrained into a linear shape by external force so as to be conveyed to the lungs of a human or an animal body for release. However, when an implant is loaded by an existing conveyor, the curled implant needs to be placed into a tubular preloading device for auxiliary loading, which is complicated in the operation and needs an auxiliary tool.

SUMMARY

Therefore, it is necessary to provide a conveyor to simply and conveniently load and release an implant, aiming at the technical problem that the existing conveyors have complicated operation in loading an implant and require auxiliary tools.

Thus, embodiments include a conveyor for an implant having at least one cavity, including a conveying handle, a conveying cable and a core wire, the conveying cable being a tubular body, a proximal end of the core wire being connected to the conveying handle, and a distal end of the core wire penetrating through a distal end of the conveying cable from a proximal end of the conveying cable, where a first control is provided on the conveying handle, and when the implant is connected to the distal end of the conveying cable, the first control controls the distal end of the core wire to extend into the implant to straighten the implant of a preset shape, or the first control controls the core wire to withdraw from the implant to restore the implant to the preset shape.

In one embodiment, where the first control includes a first key and a guide rail, and the first key is sleeved outside the guide rail and is slidable along an axial direction of the guide rail, and the proximal end of the core wire is connected to the first key.

In one embodiment, where the portion of the first key in contact with the guide rail is provided with a ball member, and a plurality of first protrusions are provided at intervals along an axial direction of the guide rail on at least a surface of the guide rail in contact with the first key, and the ball member cooperates with the first protrusions to make a sound when the first key slides along the guide rail.

In one embodiment, where the conveying handle is further provided with a second control, and the core wire cannot move relative to the conveying cable in the conveying cable when the core wire is locked by the second control; when the core wire is unlocked by the second control, the core wire can be controlled to move relative to the conveying cable in the conveying cable through the first control.

In one embodiment, where the second control includes a knob, a locking seat and a locking block, and the locking seat is an annular body having an opening, and the core wire extends through the locking seat, and the locking block can extend into the locking seat from the opening, and the knob is an annular body and sleeved outside both the locking seat and the locking block; the knob includes a first rotating area and a second rotating area which are connected, an inner diameter of the first rotating area is larger than an inner diameter of the second rotating area, and when the knob is rotated to make the locking block contact with an inner wall of the second rotating area, the locking block locks the core wire on an inner wall of the locking seat; when the knob is rotated so that one end of the locking block which is far away from the core wire corresponds to an inner wall of the first rotating area, no interaction force exists between the core wire and the locking seat.

In one embodiment, where the conveying handle is further provided with a third control, the distal end of the core wire is always closer to the distal end of the implant than the distal end of the conveying cable when the third control is in a locked state and the first control controls the core wire to move within the implant; when the third control is in an unlocked state and the first control controls the core wire to be completely extracted out from the implant, the implant is released and in the preset shape.

In one embodiment, where the third control includes a second key, a prying section and a first elastic component, and one end of the prying section abuts against the second key and the other end is connected to one end of the first elastic component, and the other end of the first elastic component is fixed on an inner wall of the conveying handle, and a prying fulcrum of the prying section is fixed on the inner wall of the conveying handle; when the second key is not pressed, the first elastic component is in a compression state, and the end of the prying section connected to the first elastic component blocks the first control from controlling the core wire to move towards the proximal end of the conveying handle under an anti-compression effect of the first elastic component; and when the second key is pressed, the end of the prying section connected to the first elastic component is pried to further compress the first elastic component so as to release the restriction of the third control on the first control to control the movement of the core wire towards the proximal end of the conveying handle.

In one embodiment, where the conveying handle is further provided with a fourth control and a plurality of gears, the maximum distance that the distal end of the core wire is controlled by the first control to pass out of the distal end of the conveying cable is defined when the fourth control coordinates with the gears.

In one embodiment, where for each of the gears, a second protrusion is correspondingly provided on an inner wall of the conveying handle, and the fourth control includes a third key, a clamping block and a limiting block, and the clamping block is provided with first grooves cooperating with the second protrusions, and one side, opposite to the first grooves, of the clamping block is provided with a plurality of second grooves, and one side of the limiting block is provided with third protrusions cooperating with the second grooves, and the distal end of the other side of the limiting block is provided with a fourth protrusion, and the clamping block is connected to the limiting block through at least one second elastic component; when the third key is not pressed, the second protrusions are clamped with the first grooves; when the third key is pressed until the second protrusions are extracted from the first grooves, the second grooves of the clamping block are clamped with the third protrusions of the limiting block, and the clamping block and the limiting block move along with the movement of the third key.

In one embodiment, where the fourth control includes a fourth key and a gear baseboard, and the middle of the fourth key is fixed on the conveying handle; two ends of one side, opposite to the gear baseboard, of the fourth key are respectively provided with a limiting boss, and one side, opposite to the fourth key, of the gear baseboard is provided with at least two third grooves, and the fourth key is connected to the gear baseboard through a limiting member cooperating with the third grooves; and the fourth key limits a distance that the core wire is controlled by the first control to pass out of the distal end of the conveying cable by controlling the matching of the limiting member with different third grooves.

In one embodiment, where the limiting member includes a fixing tube, a third elastic component and a ball, and one end of the fixing tube is fixed on the fourth key and positioned between the two limiting bosses, and the third elastic component is received in the fixing tube, with one end connected to the fourth key and the other end connected to the ball; and the third elastic component is in a compressed state, so that the ball is pressed against the third grooves of the gear baseboard and partially received in the fixing tube.

In one embodiment, where the limiting member includes a blind tube and a fourth elastic component, and the bottom of the blind tube is bulb-shaped, and the fourth elastic component is partially received in the blind tube, and one end of the fourth elastic component received in the blind tube is connected to the bottom of the blind tube, and the other end is connected to the fourth key.

In the conveyor, when the implant having at least one cavity is connected to the distal end of the conveying cable, the first control controls the distal end of the core wire to extend into the implant to straighten the implant with a preset shape, or the first control controls the core wire to withdraw from the implant to release the straightened implant and enable the implant to restore the preset shape, and the movement of the core wire in a channel formed after the conveying cable and the implant are connected is controlled through the first control, so that the conveyor can simply and conveniently load and release the implant on the conveyor without any other auxiliary tool required, and can be used in the entire implantating process of loading, conveying, release and recovery the implant.

DETAILED DESCRIPTION OF EMBODIMENTS

In order to make the purposes, technical solutions, and advantages of the embodiments more fully apparent, further details are set forth with reference to the accompanying drawings and embodiments. It can be appreciated that the embodiments described herein are merely illustrative and are not intended to be limiting.

It can be noted that in the field of interventional medicine, an end of the instrument that is closer to an operator is generally referred to as a proximal end of the instrument, another end of the instrument that is farther from the operator is referred to as a distal end of the instrument, and the distal and proximal ends of various components of the instrument are defined in the same manner.

Hereinafter, technical solutions will be described in further detail with reference to specific embodiments.

Embodiment 1

According to embodiment 1, a conveyor for an implant having at least one cavity includes a conveying handle, a conveying cable and a core wire, the conveying cable being a tubular body, a proximal end of the core wire being connected to the conveying handle, a distal end of the core wire penetrating a distal end of the conveying cable from a proximal end of the conveying cable. The implant may be a lung volume reduction implant, and after implantation and release of the implant into the lung by the conveyor, the implant returns from a straight line in the conveying state to a preset shape in a natural state, thereby compressing lung tissue and further reducing lung volume. For example, the preset shape is a curled shape.

Figure 1:
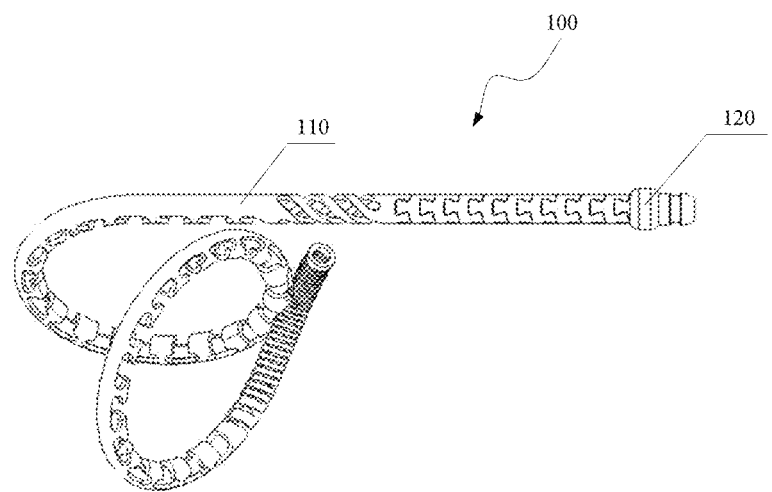
FIG. 1 is a structural schematic diagram of an implant to be conveyed by a conveyor of embodiment 1.

Referring to FIG. 1, the implant 100 in embodiment 1 includes an implant matrix 110 and a connector 120. The implant matrix 110 is a spatially geometrically curled body in its natural state. The implant matrix 110 is shaped into a spatially geometrically curled body from a memory alloy tube, such as a nickel-titanium tube, by laser cutting, heat treatment, or other processes. Since the memory alloy is super-elastic and the implant matrix 110 is a hollow tubular body, the implant matrix 110 can be straightened from a curled state to a straight state after a linear metal wire having a certain bending strength is inserted into the implant matrix 110, and the implant matrix 110 returns to the curled state in the natural state from the straight state after the metal wire is withdrawn.

Figure 2:
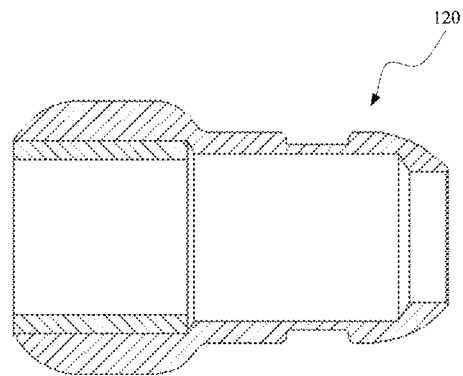
FIG. 2 is a side sectional view of a connector of the implant in FIG. 1.

Referring to FIG. 2, the connector 120 of the implant 100 is a hollow tubular body made of a biocompatible metal or polymer material by machining, 3D printing, powder metallurgy, die-casting, or the like. The implant matrix 110 and the connector 120 may be connected by an interference fit, laser welding, bonding, or the like. A proximal end of the connector 120 is bulbous as an example so as to facilitate the insertion into a closing-in steel bushing 210 of the conveying cable 200.

Figure 3:
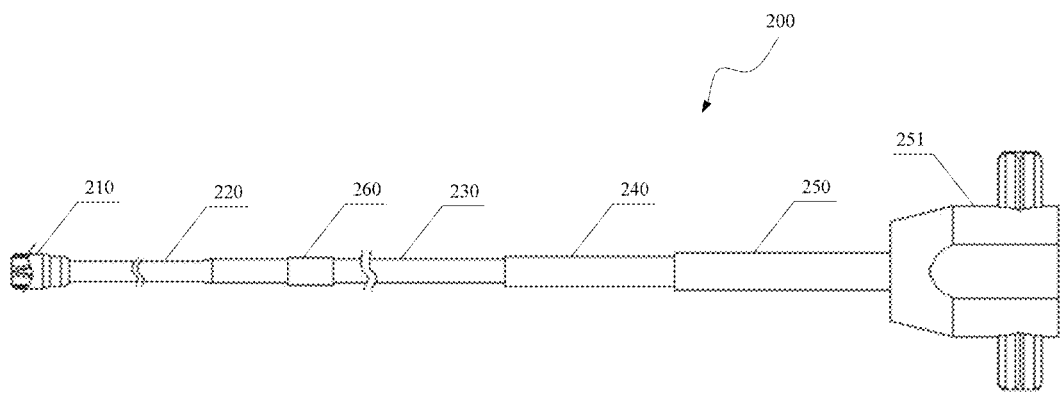
FIG. 3 is a structural schematic diagram of a conveying cable of the conveyor of embodiment 1.
Figure 4:
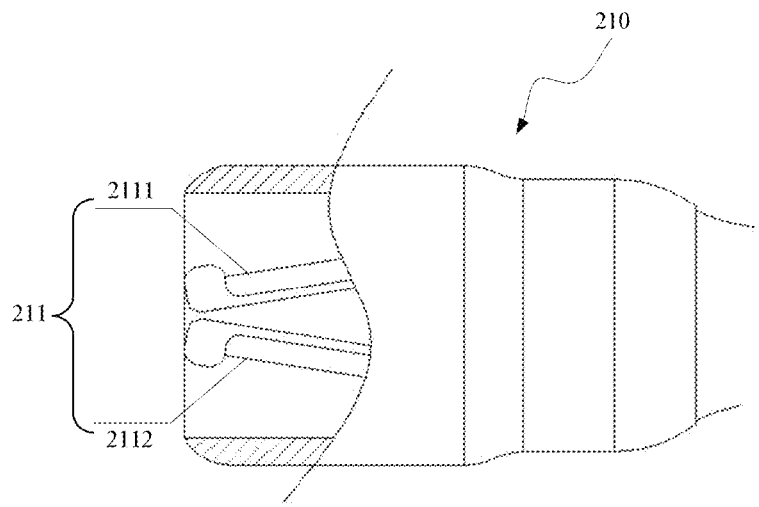
FIG. 4 is a side sectional view of a closing-in steel bushing of the conveying cable in FIG. 3.

Referring to FIG. 3, the conveying cable 200 includes, from the distal end to the proximal end, the closing-in steel bushing 210, a grinding section 220, a spring tube 230, a connecting tube 240, and a nozzle 250. The closing-in steel bushing 210 is formed into a tubular structure from a metal material by machining, and reference is made to FIG. 4, which is a cross-sectional diagram taken along an axial direction thereof, and has several steps and rounded chamfers at both ends. A clamping head 211 is provided inside the closing-in steel bushing 210, and the clamping head 211 is made of a super-elastic alloy material through machining and heat setting. The clamping head 211 includes a first clamping rod 2111 and a second clamping rod 2112, the distal ends of the first clamping rod 2111 and the second clamping rod 2112 are close to each other in an initial state, the proximal ends of the first clamping rod 2111 and the second clamping rod 2112 are respectively fixed on an inner wall of the closing-in steel bushing 210, and a maximum outer diameter of the whole formed by the first clamping rod 2111 and the second clamping rod 2112 in the initial state (that is, without external force) is smaller than an inner diameter of a proximal end of a tubular body of the connector 120 of the implant 100. The wall thickness of the grinding section 220 is less than the wall thickness of the spring tube 230, enabling a tubular body at the distal end of the conveying cable 200 to be more flexible to enhance the pass-through performance of the conveying cable 200. The spring tube 230 is formed by winding a plurality of stainless steel wires. The connecting tube 240 may be made of an off-the-shelf metal tube or a polymer tube by machining, an inner diameter of which is greater than a maximum outer diameter of the core wire. The nozzle 250 is an injection molded member or a hardware rubber-coated member, and a proximal end of the nozzle 250 is provided with a connecting base 251 to connect the conveying cable 200 and the conveying handle together. One or more sections of 5-50 mm colored marking tape 260 are provided on the spring tube 230, a distance between the marking tape 260 and the distal end of the conveying cable 200 being 400-900 mm. The spring tube 230 may be blackened or blued to form the marking tape 260, or a section of colored polymer material may be attached by adhesive or hot melt for marking to indicate to an operator the length of the conveying cable 200 into a human or animal body.

Figure 5:
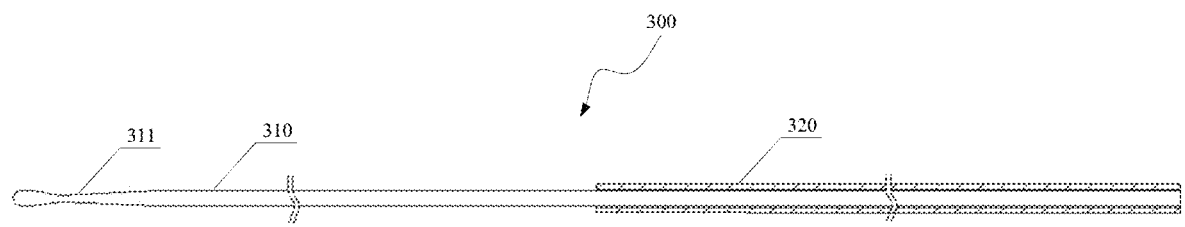
FIG. 5 is a structural schematic diagram of a core wire of the conveyor of embodiment 1.

Referring to FIG. 5, the core wire 300 includes a metal rod 310 and a reinforcing tube 320, and the reinforcing tube 320 is sleeved on a proximal end section of the metal rod 310. In order for the core wire 300 to better support the implant 100 from being curled to being straight, a guide section 311 having a bending resistance gradually increased from an intermediate section to both ends may be provided at a distal end of the core wire 300. A diameter of a distal end of the guide section 311 is the same as a diameter of a main body portion of the core wire 300, the diameter of the distal end of the guide section 311 to the intermediate section of the guide section 311 is gradually reduced, and the diameter of the intermediate section of the guide section 311 to a proximal end of the guide section 311 is gradually increased until the diameter is increased to be the same as the diameter of the main body portion of the core wire 300. The reinforcing tube 320 is sleeved on the proximal end section of the metal rod 310 to reinforce the strength of the proximal end section of the metal rod 310, and is usually made of a metal tube or a polymer tube. The metal rod 310 and the reinforcing tube 320 can be connected by welding or bonding, where a diameter of the metal rod 310 is 0.5-1.5 mm, and an outer diameter of the reinforcing tube is 0.8-2.5 mm.

Figure 6:
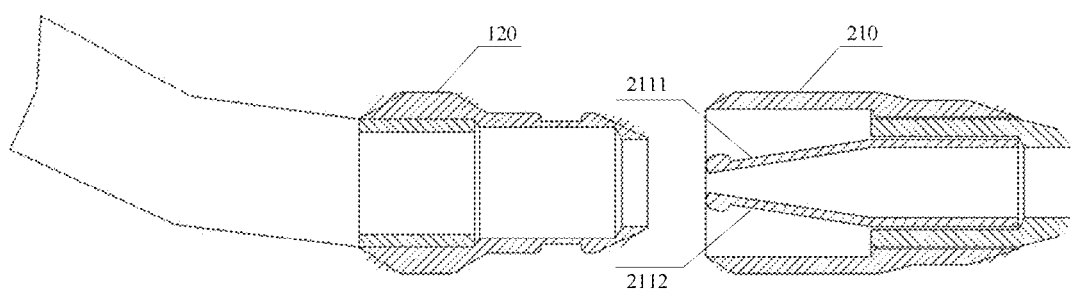
FIG. 6 is a schematic diagram of the conveying cable of the conveyor of embodiment 1 when not connected to the implant.
Figure 7:
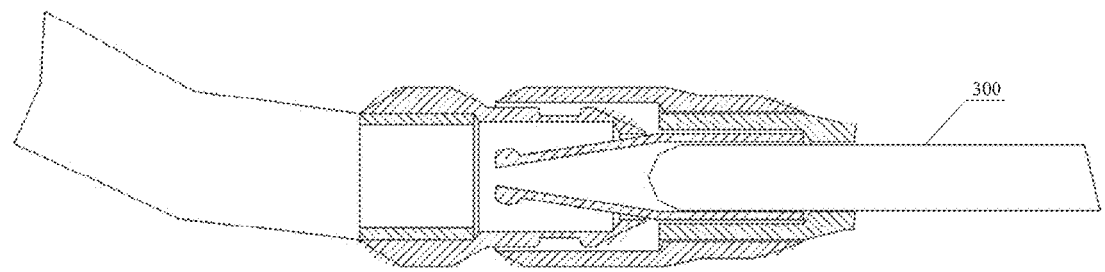
FIG. 7 is a partial schematic diagram of the conveyor in embodiment 1 when the connector of the implant is inserted into the closing-in steel bushing of the conveying cable.
Figure 8:
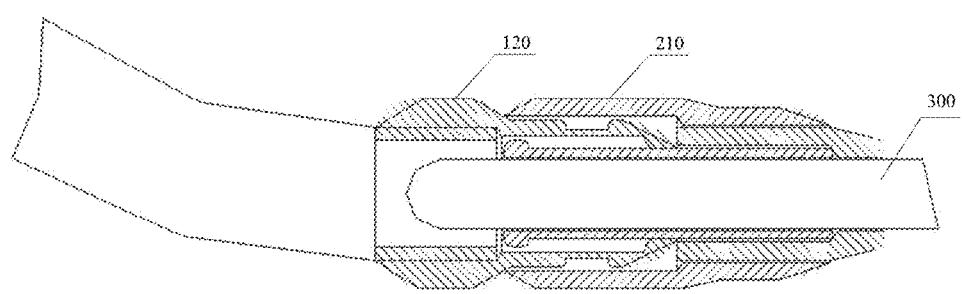
FIG. 8 is a partial schematic diagram of the conveyor in embodiment 1 when the connector of the implant is inserted into and connected to the closing-in steel bushing of the conveying cable.

Referring collectively to FIGS. 6-8, the connector 120 is inserted into the closing-in steel bushing 210 and the connection of the implant 100 to the conveying cable 200 is achieved after the core wire 300 passes out of the distal end of the conveying cable 200. At this time, the core wire 300 respectively distracts the first clamping rod 2111 and the second clamping rod 2112 towards the inner wall of the closing-in steel bushing 210, and the first clamping rod 2111 and the second clamping rod 2112 constitute an outer diameter larger than an inner diameter of the proximal end of the tubular body of the connector 120 of the implant 100 but smaller than the inner diameter of the distal end of the tubular body. Thereafter, the core wire 300 is controlled to continue to penetrate into the implant 100 so that the implant 100 can be changed from a curled shape to a straight shape.

Figure 9:
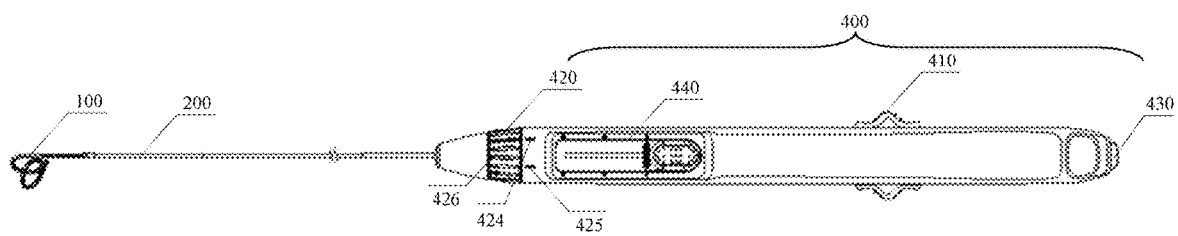
FIG. 9 is a schematic diagram showing the appearance of the conveyor in embodiment 1 after being connected to the implant.
Figure 10:
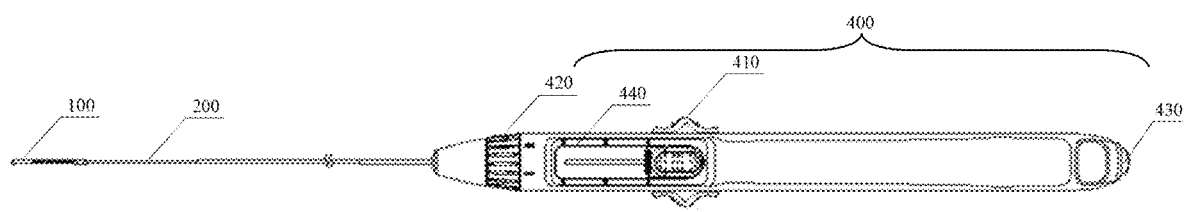
FIG. 10 is a schematic diagram of the conveyor in embodiment 1 when the implant is straightened from a curled shape to a straight line.
Figure 11:
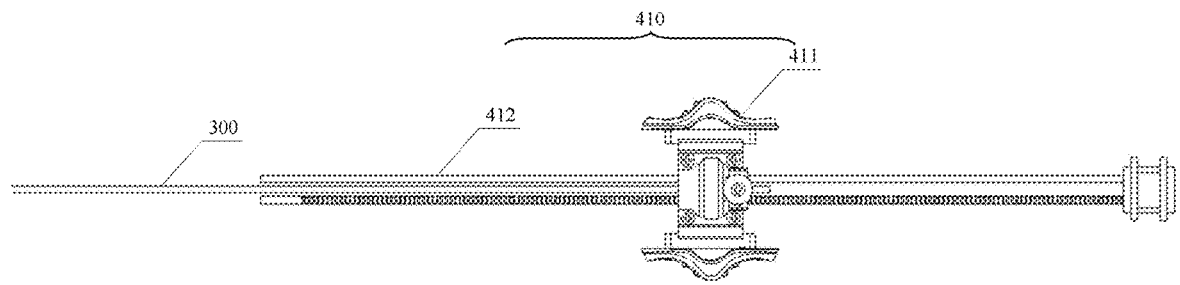
FIG. 11 is a structural schematic diagram of a first control of the conveyor of embodiment 1.
Figure 12:
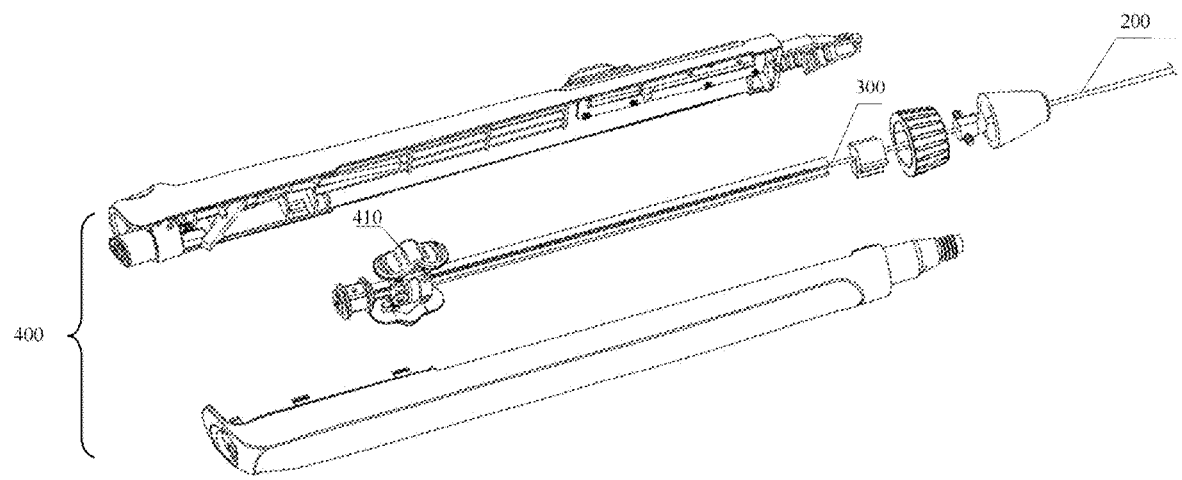
FIG. 12 is an assembling exploded diagram of the conveyor of embodiment 1.

Referring collectively to FIGS. 9-10, a conveying handle 400 of embodiment 1 is provided with a first control 410 that controls the distal end of the core wire 300 (not shown) to extend into the implant 100 to straighten the curled implant 100 when the hollow implant 100 is connected to the distal end of the conveying cable 200, thereby enabling the loading of the implant 100 on the conveyor. The first control 410 can further control the withdrawal of the core wire 300 from the implant 100 to release the straightened implant 100 and restore the implant 100 to the curled shape, thereby effecting the release of the implant 100 at a target lesion. For example, referring to FIG. 11, the first control 410 includes a first key 411 and a guide rail 412 which is a hollow body composed of upper and lower rods. The first key 411 is sleeved on an outer side of the guide rail 412 and is axially slidable along the guide rail 412, and the proximal end of the core wire 300 extends from a distal end of the guide rail 412 into an interior of the guide rail 412 and is connected to the first key 411. The core wire 300 and the first key 411 may be press-connected by a screw, or fixed together by welding or bonding. A linear motion mode of the first key 411 on the guide rail 412 may be a screw-nut mechanism or a rack-and-pinion mechanism, etc., which is not limited herein. An exploded view of the assembly of the conveying handle 400 with the core wire 300 and the conveying cable 200 is shown in FIG. 12. It can be appreciated that in other embodiments, the guide rail 412 may consist of only one rod, or the guide rail 412 may be a tubular hollow body.

By controlling the travel of the core wire 300 in the channel formed by the connection of the conveying cable 200 with the implant 100, the first control 410 provided on the conveyor can simply and conveniently realize the loading and releasing of the implant 100 on the conveyor, and can be used in the entire implantation process of loading, conveying, releasing and recovering the implant 100. The implant 100 can be loaded without an aid of other loading tools, and the loading of the implant 100 can be accomplished by simply inserting the connector 120 of the implant 100 into the closing-in steel bushing 210 of the conveying cable 200, and then controlling the insertion of the core wire 300 into the implant 100 through the first control 410. The loaded implant 100 is constrained into a straight line by the core wire 300 so that the conveying of the implant 100 can be continued by the conveyor. After the implant 100 is conveyed to a target location, the release of the implant 100 is achieved by controlling the withdrawal of the core wire 300 from the implant 100 into the conveying cable 200 via the first control 410. When the implant 100 is to be retrieved, the connector 120 of the implant 100 may be inserted into the closing-in steel bushing 210 of the conveying cable 200 by other means, and then the core wire 300 may be controlled by the first control 410 to be inserted into the implant 100 so that the implant 100 is in a straight line, and the implant 100 may be retrieved by withdrawing the conveyor.

Figure 13:
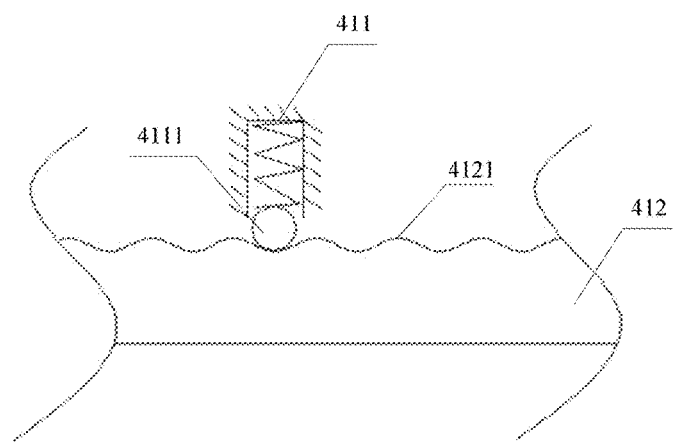
FIG. 13 is a schematic diagram when a ball member of the first key of the conveyor of embodiment 1 coordinates with a guide rail.

Further, referring to FIG. 13, the portion of the first key 411 in contact with the guide rail 412 is provided with a ball member 4111, which is a ball as an example, and a plurality of first protrusions 4121 are provided at intervals along the axial direction of the guide rail 412 on at least the surface of the guide rail 412 in contact with the first key 411, and when the first key 411 slides along the guide rail 412, the ball member 4111 cooperates with the first protrusions 4121 to make a sound, so that the use experience of operating the conveying handle can be improved.

For example, the conveying handle 400 in the embodiment is further provided with a second control 420, and when the second control 420 controls the core wire 300 to be static relative to the conveying handle 400, the core wire 300 cannot move in the conveying cable 200, and the core wire 300 is in a locked state; when the second control 420 does not control the core wire 300 to be static relative to the conveying handle 400, the core wire 300 is in an unlocked state, where upon the core wire 300 can be controlled to move relative to the conveying handle 400 in the conveying cable 200 by the first control 410.

Figure 14:
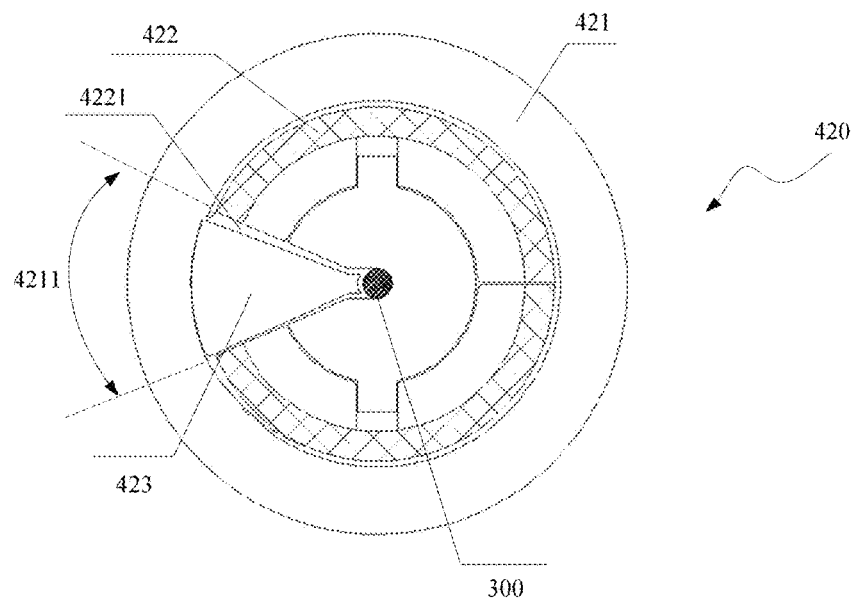
FIG. 14 is a front sectional diagram of a second control of the conveyor of embodiment 1.

For example, referring collectively to FIG. 9 and FIG. 14, the second control 420 includes a knob 421, a locking seat 422 which is a ring-shaped body having an opening 4221 on a side surface and through whose cavity the core wire 300 passes, and a locking block 423 which extends from the opening 4221 into the locking seat 422, the knob 421 being an annular body and sleeved outside both the locking seat 422 and the locking block 423. The knob 421 includes a first rotating area 4211 and a second rotating area 4212 (not shown, namely, a portion of the knob 421 except for the first rotating area 4211) which are connected, and an inner diameter of the first rotating area 4211 is larger than an inner diameter of the second rotating area 4212 on the basis of a circle center of the knob 421. When the knob 421 is rotated to make the locking block 423 contact with an inner wall of the second rotating area 4212, the core wire 300 is locked on an inner wall of the locking seat 422 by the locking block 423, and when the knob 421 is rotated to make an end of the locking block 423 far away from the core wire 300 correspond to an inner wall of the first rotating area 4211, there is no interaction force between the core wire 300 and the locking seat 422, that is, the core wire 300 and the locking seat 422 are in contact but have no interaction force with each other, or the core wire 300 is completely separated from the locking seat 422.

Referring to FIG. 9 again, the second control 420 is provided at the distal end of the conveying handle 400 with a mark 424 and a mark 425 provided at the position closer to knob 421 on the conveying handle 400 and with a mark 426 provided on the knob 421. When the knob 421 is rotated until the mark 426 on the knob 421 is aligned with the mark 424 on the conveying handle 400, the core wire 300 is bound between the inner wall of the locking seat 422 and the locking block 423, and the core wire 300 needs to move against the frictional force generated by the pressing of the inner wall of the locking seat 422 and the locking block 423 against the core wire 300, so that the core wire 300 is locked on the inner wall of the locking seat 422 by the locking block 423, where upon the core wire 300 (not shown) cannot move within the conveying cable 200 through the first control 410. When the knob 421 is rotated until the mark 426 on the knob 421 is aligned with the mark 425 on the conveying handle 400, the core wire 300 is released from the restraint between the inner wall of the locking seat 422 and the locking block 423, where upon the movement of the core wire 300 within the conveying cable 200 can be controlled by the first control 410.

By providing the second control 420 on the conveying handle 400, it is ensured that the implant 100 is continuously kept in a straight line after being straightened by the core wire 300, so that the safe conveying of the implant 100 by the conveyor is facilitated, and early release of the implant 100 when the implant 100 does not reach a designated position due to misoperation during conveying is avoided.

It can be appreciated that, in other embodiments, the second control 420 may not be provided on the conveying handle 400, so long as the first control 410 can control the movement of the core wire 300.

For example, in the embodiment, a third control 430 is further provided on the conveying handle 400, and when the first control 410 controls the core wire 300 to move within the implant 100, the distal end of the core wire 300 is closer to the distal end of the implant 100 than the distal end of the conveying cable 200, whereupon the implant 100 cannot be released, and the third control 430 is initially locked; when the third control 430 is operated to enable the first control 410 to control the complete withdrawal of the core wire 300 from the implant 100, the third control 430 is in an unlocked state, and the implant 100 is released and curled. The third control 430 may operated to allow it to switch between a locked state and an unlocked state.

Figure 15:
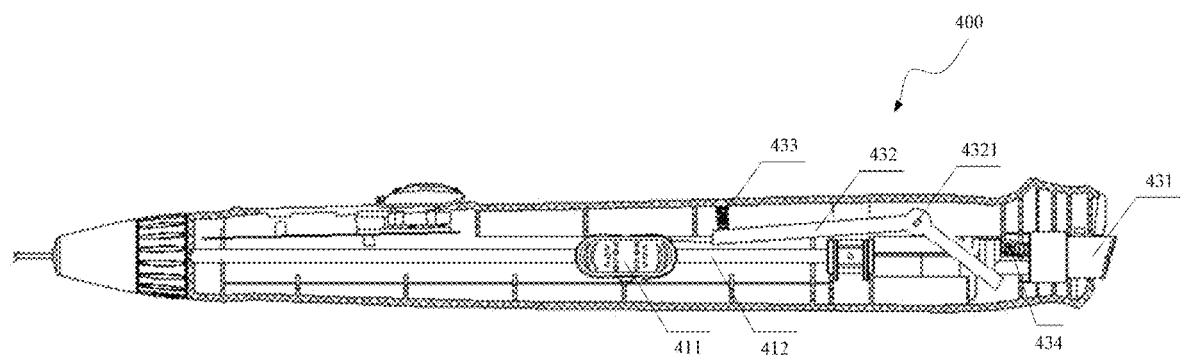
FIG. 15 is a side sectional diagram of a conveying handle of the conveyor of embodiment 1.

For example, referring to FIG. 15, the third control 430 includes a second key 431, a prying section 432 and a first elastic component 433. One end of the prying section 432 abuts against the second key 431, and the other end thereof is connected to one end of the first elastic component 433, and the other end of the elastic component 433 is fixed on the inner wall of the conveying handle 400, and a prying fulcrum 4321 of the prying section 432 is fixed on the inner wall of the conveying handle 400; when the second key 431 is not pressed, the first elastic component 433 is in a compressed state, and one end of the prying section 432 connected to the first elastic component 433 blocks the first control 410 (not shown) from controlling the core wire 300 (not shown) to move towards the proximal end of the conveying handle 400 under the anti-compression effect of the first elastic component 433; and when the second key 431 is pressed, one end of the prying section 432 connected to the first elastic component 433 is pried to move towards the inner wall of the conveying handle 400 and further compress the first elastic component 433, thereby releasing the restriction of the third control 430 on the first control 410 to control the movement of the core wire 300 towards the proximal end of the conveying handle 400. The first elastic component 433 is a spring as an example.

When the second key 431 is not pressed, the third control 430 is in a locked state, and one end of the prying section 432 connected to the first elastic component 433 is pressed against the guide rail 412 of the first control 410 under the anti-compression effect of the first elastic component 433, so that the movement of the first key 411 towards the proximal end is prevented, where upon the first key 411 cannot move to the terminal position of the proximal end of the guide rail 412 along the guide rail 412, such that the core wire 300 cannot move to the terminal position of the proximal end of the guide rail 412 along with the first key 411, and the terminal position of the proximal end of the guide rail 412 is the farthest point where the proximal end of the core wire 300 moves proximally in the axial direction, and the implant 100 can be released only if the proximal end of the core wire 300 reaches the terminal position of the proximal end of the guide rail 412, i.e., the core wire 300 is completely withdrawn from the implant 100. Before the proximal end of the core wire 300 reaches the terminal position of the proximal end of the guide rail 412, i.e., when the core wire 300 has not been completely withdrawn from the implant 100, operation may still continue to straighten the implant 100 by sliding the first key 411 towards the distal end.

When the second key 431 is pressed until one end of the prying section 432 connected to the first elastic component 433 moves towards the inner wall of the conveying handle 400 and no longer obstructs the axial movement of the first key 411, the third control 430 is in the unlocked state, and a fifth elastic component 434 provided inside the conveying handle 400 and connected to the second key 431 is compressed, meanwhile the second key 431 pushes one end of the prying section 432 connected to the second key 431 to move in the direction away from the second key 431. Under an action of the prying fulcrum 4321, the end of the prying section 432 connected to the first elastic component 433 moves in the direction away from the guide rail 412 so as to release the obstruction of the movement of the first key 411 towards the proximal end, where upon the first key 411 can drive the core wire 300 to move to the terminal position of the proximal end of the guide rail 412, so as to release the connector 120 of the implant 100 from being connected to the closing-in steel bushing 210 of the conveying cable 200 and further release the implant 100. After releasing the second key 431, the fifth elastic component 434 returns and drives the second key 431 to move to a position before being pressed. The fifth elastic component 434 is a spring as an example.

It can be noted that a distance L1 between the end of the prying section 432 connected to the first elastic component 433 and the terminal of the proximal end of the guide rail 412 may be determined according to a minimum distance L2 of the movement of the core wire 300 in the process of changing the connector 120 of the implant 100 and the closing-in steel bushing 210 of the conveying cable 200 from a connected state to a disconnected state, and L1 is greater than or equal to L2.

The third control 430 is provided on the conveying handle 400 to limit the farthest position of the core wire 300 towards the proximal end when the implant 100 is not released, thereby avoiding the release of the implant 100 due to misoperation when the implant 100 is not confirmed to be released, and only when the third control 430 is in an unlocked state can the implant 100 be released successfully, which improves the safety of the implant 100 during the implantation process.

It can be appreciated that, in other embodiments, the third control 430 may not be provided on the conveying handle 400, so long as the first control 410 can control the movement of the core wire 300.

Further, a fourth control 440 and a plurality of gears 451 are provided on the conveying handle 400, where different gears 451 are at different distances from the terminal of the distal end of the conveying handle 400, and the fourth control 440 is configured to select an appropriate gear 451 to define the maximum distance that the distal end of the core wire 300 passes out of the distal end of the conveying cable 200.

Since the anatomical structure of a human lung is relatively complicated, there are correspondingly a plurality of implants 100 of different sizes, the implants 100 of the different sizes vary in lengths after the implants 100 are straightened out from a spatial curled shape, and the lengths after being straightened out are generally 50-200 mm Different gears 451 are provided on the conveying handle 400, and when the fourth control 440 coordinates with a certain gear 451, the maximum distance of the distal end of the core wire 300 being controlled by the first control 410 to pass out of the distal end of the conveying cable 200 is defined, so as to make the conveyor only load the implants 100 matched with the corresponding gears 451 according to the difference of the gears 451 set on conveyor.

Figure 16:
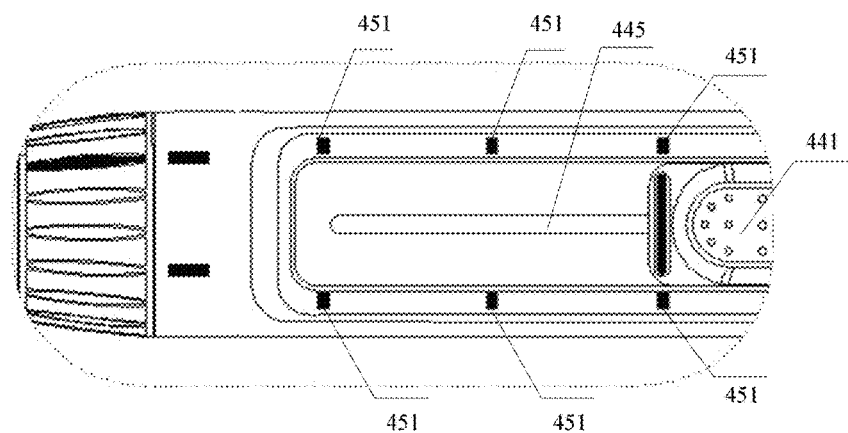
FIG. 16 is a partial schematic diagram showing the appearance of the conveyor of embodiment 1 in which gears are provided.
Figure 17:
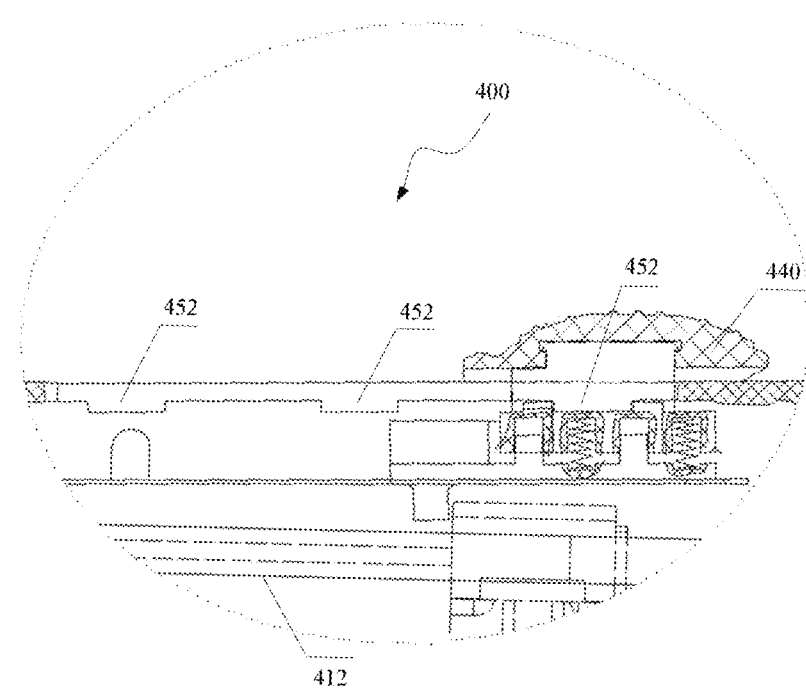
FIG. 17 is a schematic diagram of a fourth control of the conveyor of embodiment 1.
Figure 18:
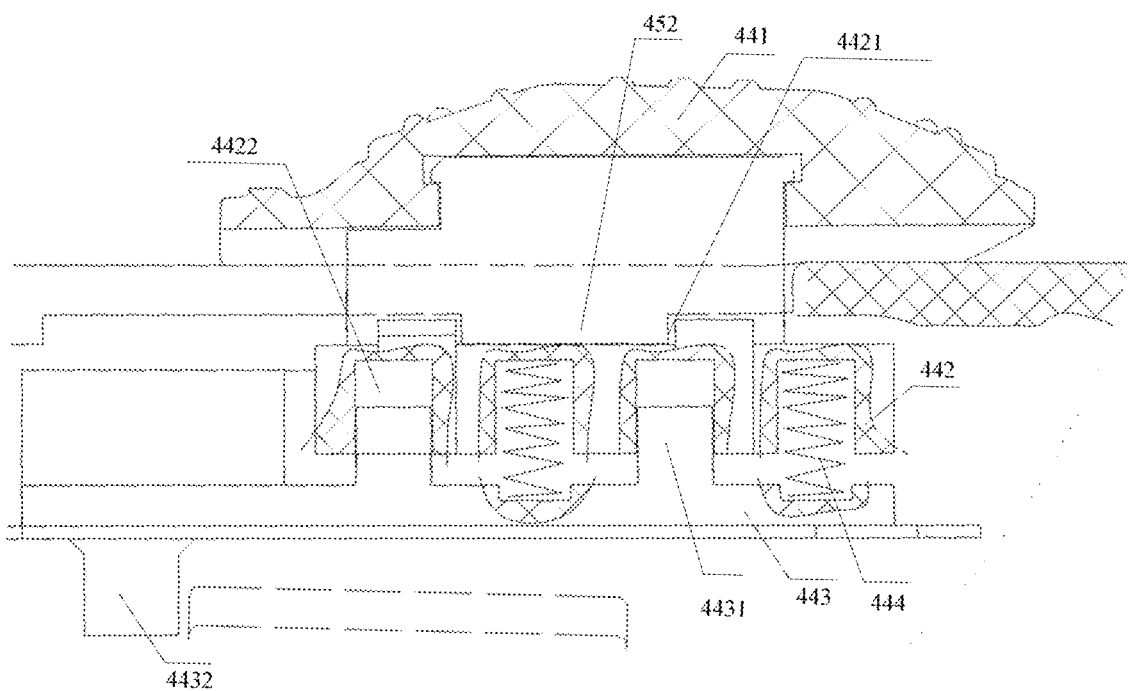
FIG. 18 is a schematic diagram of the fourth control of the conveyor of embodiment 1 when selecting one of the gears.

For example, referring collectively to FIGS. 16-18, for each gear 451 provided on the conveying handle 400, a second protrusion 452 is provided on the inner wall of the conveying handle 400, the fourth control 440 (not shown) includes a third key 441, a clamping block 442 and a limiting block 443, and the clamping block 442 is provided with first grooves 4421 cooperating with the second protrusions 452, and a plurality of second grooves 4422 are provided on one side, opposite to the first grooves 4421, of the clamping block 442. Third protrusions 4431 matching with the second grooves 4422 are provided on one side of the limiting block 443, and a fourth protrusion 4432 is provided at the distal end of the other side of the limiting block 443, and the clamping block 442 and the limiting block 443 are connected through at least one second elastic component 444. For example, the conveying handle 400 is provided with three gears 451, and correspondingly, the inner wall of the conveying handle 400 is provided with three second protrusions 452. For example, the clamping block 442 is provided with four second grooves 4422, and the limiting block 443 is provided with two third protrusions 4431, and the clamping block 442 and the limiting block 443 are connected through two second elastic components 444, and the second elastic components 444 and the third protrusions 4431 are provided at intervals, and one end of the second elastic components 444 is connected to the limiting block 443 while the other end is vertically fixed in the second grooves 4422 in the clamping block 442 that does not need to cooperate with the third protrusions 4431. The fourth protrusion provided on the limiting block 443 is provided at the distal end of the limiting block 443 and pressed against the distal end of the guide rail 412 to block the movement of the first key 411 (not shown) towards the distal end as an example. The second elastic component 444 is a spring as an example.

An elongated opening 445 is provided at the proximal end of the conveying handle 400 (not shown), and different gears 451 are provided at the axial edges of the opening 445, respectively. The top of the third key 441 is positioned above the opening 445 at a distance from the opening 445, and the bottom of the third key 441 extends into the opening 445 and is connected to the clamping block 442 in a snap connection or an adhesive connection, and so on. The third key 441, connected to the clamping block 442, moves axially along the opening 445 as a whole.

Figure 19:
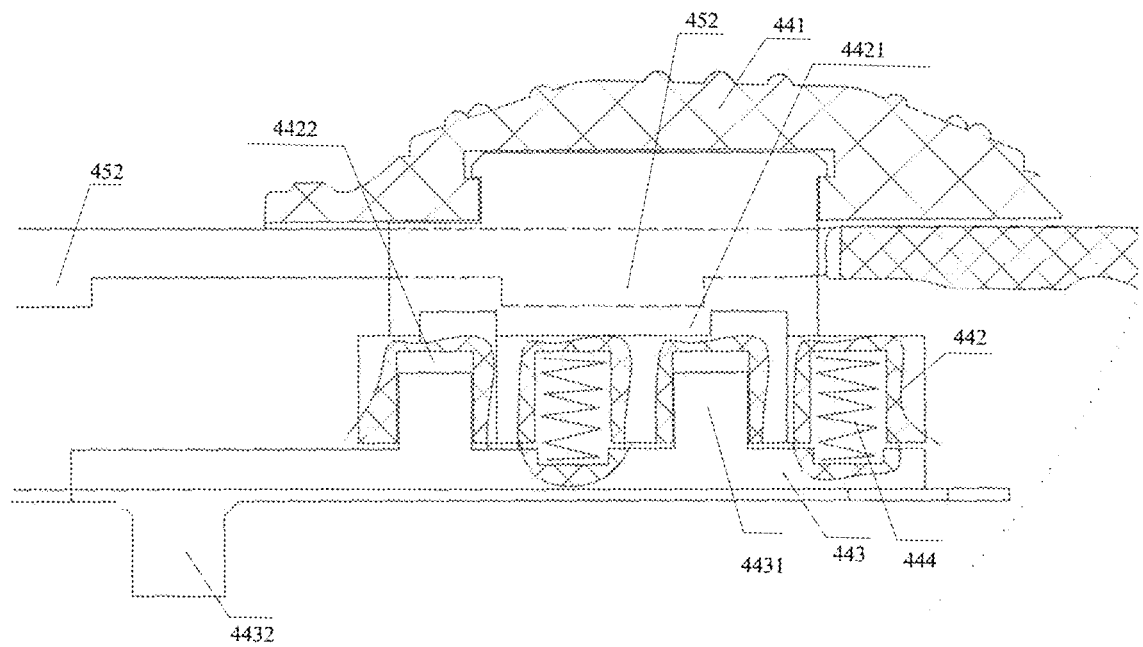
FIG. 19 is a schematic diagram of the fourth control after a third key is pressed in FIG. 18.
Figure 20:
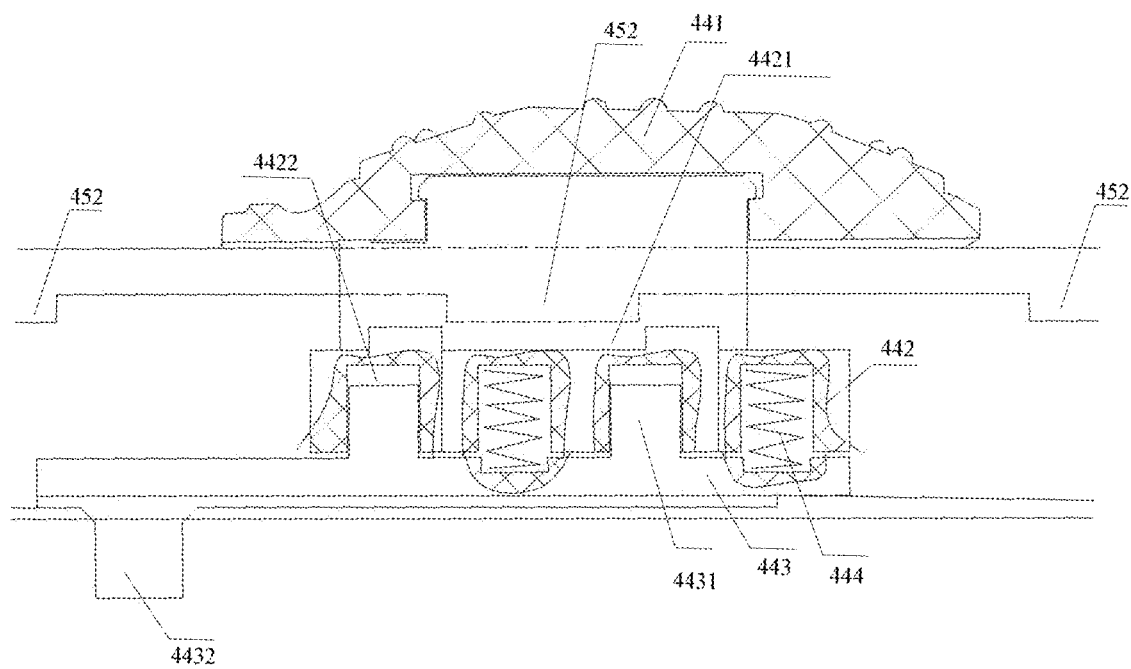
FIG. 20 is a schematic diagram of the fourth control of the conveyor of embodiment 1 when selecting another gear.
Figure 21:
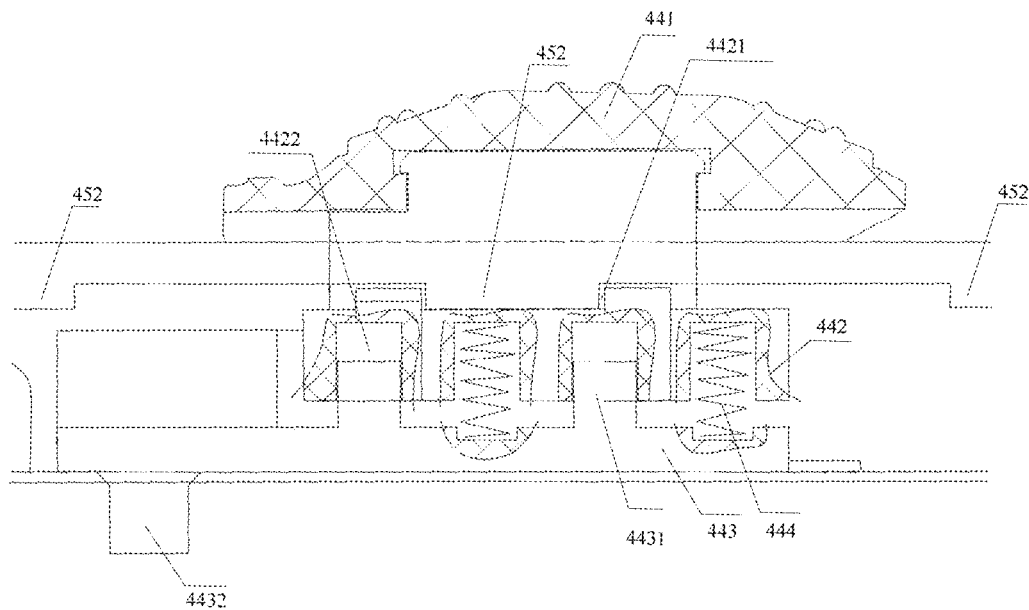
FIG. 21 is a schematic diagram of the fourth control after the third key is pressed in FIG. 20.

When the third key 441 is not pressed, the second elastic components 444 are in a compressed state, and the second protrusions 452 are engaged with the first grooves 4421 under an anti-compression action of the second elastic components 444, so that the gear 451 corresponding to the engaged second protrusions 452 is selected. Referring to FIG. 19, when the third key 441 is pressed until the second protrusions 452 withdraw from the first grooves 4421, the second grooves 4422 of the clamping block 442 are engaged with the third protrusions 4431 of the limiting block 443, and both the clamping block 442 and the limiting block 443 move along with the third key 441. Referring collectively to FIG. 20-FIG. 21, when the clamping block 442 and the limiting block 443 move to the position of the second protrusions 452 corresponding to the currently selected gear 451 as the third key 441 moves, and the first grooves 4421 and the current second protrusions 452 are engaged after releasing the third key 441, so that the gear 451 is successfully changed through the fourth control 440, that is, the maximum distance that the distal end of the core wire 300 passes out of the distal end of the conveying cable 200 is redefined.

It can be appreciated that when the farthest gear 451 is selected, the maximum distance that the distal end of the core wire 300 passes out of the distal end of the conveying cable 200 is greatest compared to the other gears 451, corresponding to the implant 100 with the maximum specification that can be loaded; when the nearest gear 451 is selected, the maximum distance that the distal end of the core wire 300 passes out of the distal end of the conveying cable 200 is the smallest compared to the other gears 451, corresponding to the implant 100 with the minimum specification that can be loaded.

It can be appreciated that in other embodiments, the fourth control 440 may not be provided on the conveying handle 400, so long as the first control 410 can control the movement of the core wire 300.

It can be appreciated that the implant having at least one cavity for conveying in the disclosure may also be a spring coil for conveying to embolism, and is not limited to the implant for lung volume reduction in this embodiment, so long as the conveyed implant is straightened by the core wire during conveying and curled after release.

Embodiment 2

Figure 22:
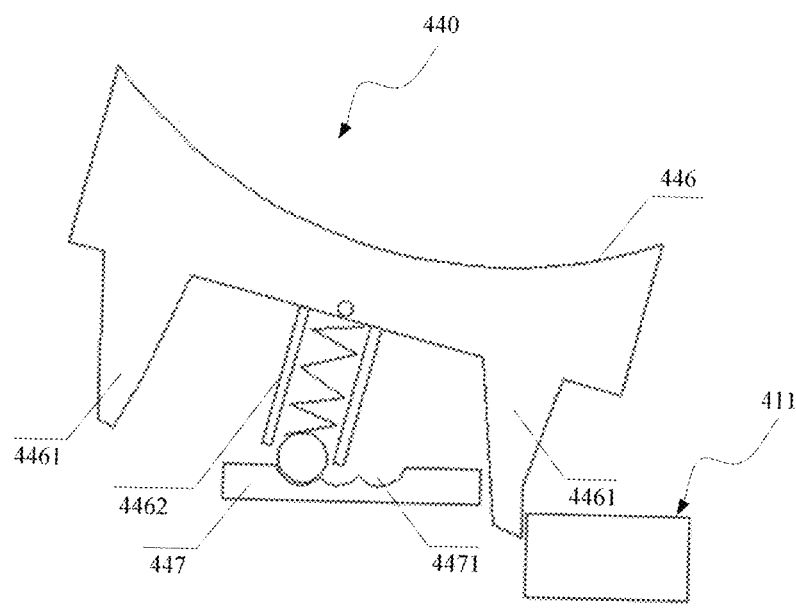
FIG. 22 is a schematic diagram of the fourth control of the conveyor of embodiment 2 when selecting the leftmost gear.

The same parts as those of embodiment 1 in embodiment 2 will not be described in detail herein. Referring to FIG. 22, the difference is mainly that the fourth control 440 includes a fourth key 446 and a gear baseboard 447, and the middle of the fourth key 446 is fixed on the conveying handle 400 (not shown), and both ends of one side, opposite to the gear baseboard 447, of the fourth key 446 are respectively provided with a limiting boss 4461. One side, opposite to the fourth key 446, of the gear baseboard 447 is provided with at least two third grooves 4471, and the fourth key 446 is connected to the gear baseboard 447 through a limiting member 4462 cooperating with the third grooves 4471; the fourth key 446 limits the distance that the core wire 300 (not shown) is controlled by the first control 410 (not shown) to pass out of the distal end of the conveying cable 200 (not shown) by controlling the matching of the limiting member 4462 with the different third grooves 4471.

Figure 23:
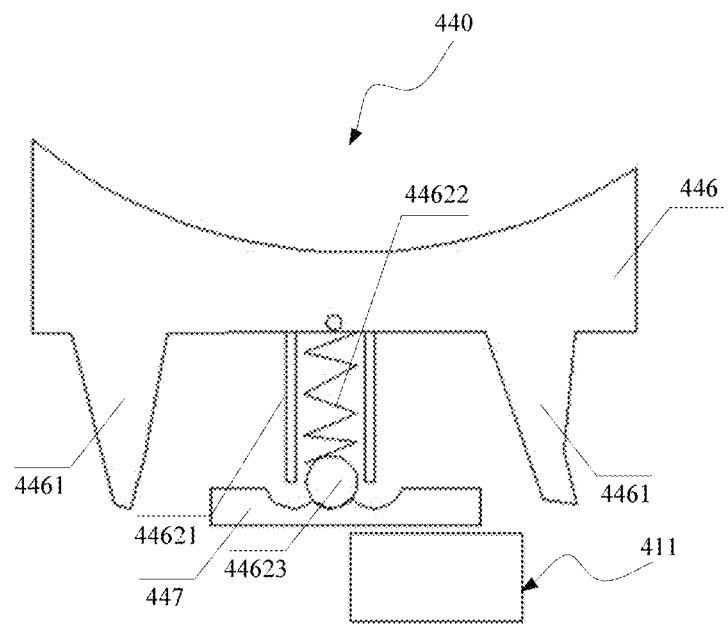
FIG. 23 is a schematic diagram of the fourth control of the conveyor of embodiment 2 when selecting the intermediate gear.

In one embodiment, an opening is provided at the proximal end of the conveying handle 400, and two different gears are provided at the axial edge of the opening and distributed at the proximal and distal ends of the opening, respectively. The top of the fourth key 446 is positioned above the opening at a distance from the opening, and the bottom of the fourth key 446 extends into the opening to be cooperatively connected to the gear baseboard 447. Three adjacent third grooves 4471 are provided on the gear baseboard 447. Referring to FIG. 23, the limiting member 4462 (not shown) includes a fixing tube 44621, a third elastic component 44622, and a ball 44623. One end of the fixing tube 44621 is fixed on the fourth key 446 and positioned in the middle of two limiting bosses 4461. The third elastic component 44622 is received in the fixing tube 44621, with one end connected to the fourth key 446, and the other end connected to the ball 44623. The third elastic component 44622 is in a compressed state such that when the limiting member 4462 is connected to the gear baseboard 447, the ball 44623 is pressed against the third grooves 4471 of the gear baseboard 447 and is partially received in the fixing tube 44621. The third elastic component 44622 is a spring as an example.

Referring to FIG. 22 again, when the ball 44623 is pressed against in the leftmost third groove 4471, the limiting boss 4461 on the left side is higher than the limiting boss 4461 on the right side, and the limiting boss 4461 on the right side blocks the first key 411 from moving towards the distal end along the guide rail 412 (not shown). That is, when the first key 411 moves to the position contacted with the limiting boss 4461 on the right side, the core wire 300 (not shown) is positioned farthest from the distal end of the conveying cable 200 (not shown). An implant 100 with the minimum specification may be loaded at the current gear.

Referring to FIG. 23 again, when the ball 44623 is pressed against the third groove 4471 of the middle position, the limiting boss 4461 on the left side is identical as the height of the limiting boss 4461 on the right side, and the limiting boss 4461 on the left side and the limiting boss on the right side 4461 fail to block the movement of the first key 411 towards the distal end along the guide rail 412 (not shown). Where upon the farthest position at which the core wire 300 (not shown) can pass out of the distal end of the conveying cable 200 (not shown) is determined by the farthest position at which the first key 411 is movable along the distal end of the guide rail 412, and since the first key 411 is movable to the terminal position of the distal end of the guide rail 412, the current gear allows loading of an implant 100 (not shown) with the maximum specification.

Figure 24:
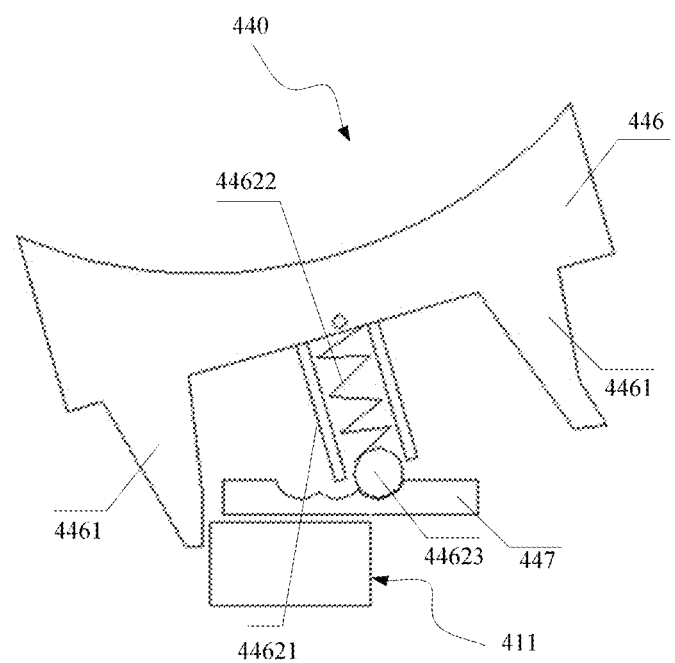
FIG. 24 is a schematic diagram of the fourth control of the conveyor of embodiment 2 when selecting the rightmost gear.

Referring to FIG. 24, when the ball 44623 is pressed against the rightmost third groove 4471, the limiting boss 4461 on the left side is lower than the limiting boss 4461 on the right side, and the limiting boss 4461 on the right side fails to block the first key 411 from moving towards the distal end along the guide rail 412 (not shown), and the limiting boss 4461 on the left side blocks the first key 411 from moving towards the distal end along the guide rail 412 (not shown), that is, when the first key 411 moves to a position in contact with the limiting boss 4461 on the left side, the core wire 300 (not shown) is at the farthest position from the distal end of the conveying cable 200 (not shown). An implant 100 (not shown) with the mediate specification may be loaded at the current gear.

In another embodiment, the limiting member 4462 includes a blind tube and a fourth elastic component. The bottom of the blind tube is bulb-shaped. The fourth elastic component is partially received in the blind tube, and one end of the fourth elastic component received in the blind tube is connected to the bottom of the blind tube, and the other end of the fourth elastic component is connected to the fourth key 446.

By taking conveying of the implant 100 in the conveying cable 200 as an example, the conveying process includes the following steps: establishing a working channel when the implant 100 is implanted through a bronchoscope, specifically, inserting a bronchoscope through the mouth or nose, and transmitting images detected by the distal end of the bronchoscope to a monitor for display after the bronchoscope is inserted into a body, so that an operator guides the distal end of the bronchoscope to enter a bronchus of a human lung; obtaining specification parameters of an implant 100 to be implanted by means of a medical imaging device and the established working channel through existing measurement techniques; inserting a conveying sheath of the conveyor into the working channel of the bronchoscope, and guiding the distal end of the conveying sheath to enter a target area in the human body; selecting an appropriate implant 100 according to the measured specification parameters of the implant 100, and sliding the fourth key 446 of the conveying handle 400 to a gear matched with the specification parameters of the selected implant 100; inserting the connector 120 of the implant 100 into the closing-in steel bushing 210 of the conveying cable 200, and pushing the first key 411 of the conveying handle 400 until the first key 411 cannot move, where upon the implant 100 is changed from a curled shape to a straight shape, so that the loading of the implant 100 is completed; rotating the knob 421 to lock the core wire 300 on the locking seat 422; inserting the loaded implant 100 into the conveying sheath, pushing the conveying cable 200 so that the implant 100 is conveyed to a specified position in the bronchus; rotating the knob 421 to unlock the core wire 300; pushing the first key 411 until the first key 411 cannot move anymore; when confirming to release the implant 100, pressing the second key 431 of the proximal end of the conveying handle 400, and then pushing the first key 411 until the first key cannot move anymore so as to complete the release of the implant 100; finally, sequentially withdrawing the conveying cable 200 and the conveying sheath to complete the implantation of the implant 100; adjusting the bronchoscope to a proper position so as to implant a next implant 100 according to the above steps; and, after completing the implantation of all implants 100, withdrawing the bronchoscope.

The various technical features of the above-mentioned embodiments may be combined in any way, and in any order, to simplify the description of embodiment, not all possible combinations of the technical features of the above-mentioned embodiments are described, however, as long as there is no conflict between these technical features, they should be considered to be within the scope disclosure.

The embodiments described above represent only a few embodiments, the description of which is specific and detailed, but should not be construed to limit the scope of the present disclosure. It can be noted that several variations and modifications may be made by those of ordinary skill in the art without departing from the spirit of the present disclosure, which all fall within the scope of the present disclosure.

The invention claimed is:

1. A conveyor for an implant having at least one cavity, comprising:
   a conveying handle, a conveying cable and a core wire, the conveying cable being a tubular body, a proximal end of the core wire connected to the conveying handle, and a distal end of the core wire penetrating through a distal end of the conveying cable from a proximal end of the conveying cable, wherein a first control is provided on the conveying handle, and when the implant is connected to the distal end of the conveying cable, the first control controls the distal end of the core wire to extend into the implant to straighten the implant of a preset shape, or the first control controls the core wire to withdraw from the implant to restore the implant to the preset shape;
   wherein the first control comprises a first key and a guide rail, and the first key is sleeved outside the guide rail and is slidable along an axial direction of the guide rail, and the proximal end of the core wire is connected to the first key; and
   wherein a portion of the first key in contact with the guide rail is provided with a ball member, and a plurality of first protrusions are provided at intervals along an axial direction of the guide rail on at least a surface of the guide rail in contact with the first key, and the ball member cooperates with the first protrusions to make a sound when the first key slides along the guide rail.

2. The conveyor for an implant having at least one cavity according to claim 1, the conveying handle is further provided with a second control, wherein the second control comprises a knob, a locking seat and a locking block, the locking seat is an annular body having an opening, the core wire extends through the locking seat, the locking block can extend into the locking seat from the opening, and the knob is an annular body and sleeved outside both the locking seat and the locking block;
   the knob comprises a first rotating area and a second rotating area which are connected, an inner diameter of the first rotating area is larger than an inner diameter of the second rotating area, and when the knob is rotated to make the locking block contact with an inner wall of the second rotating area, the locking block locks the core wire on an inner wall of the locking seat; and
   when the knob is rotated so that one end of the locking block which is far away from the core wire corresponds to an inner wall of the first rotating area, no interaction force exists between the core wire and the locking seat.

3. The conveyor for an implant having at least one cavity according to claim 1, wherein the conveying handle is further provided with a second control, the distal end of the core wire is always closer to the distal end of the implant than the distal end of the conveying cable when the second control is in a locked state and the first control controls the core wire to move within the implant; and when the second control is in an unlocked state and the first control controls the core wire to be completely extracted out from the implant, the implant is released and in the preset shape.

4. The conveyor for an implant having at least one cavity according to claim 3, wherein the second control comprises a second key, a prying section and a first elastic component, and one end of the prying section abuts against the second key and the other end is connected to one end of the first elastic component, and the other end of the first elastic component is fixed on an inner wall of the conveying handle, and a prying fulcrum of the prying section is fixed on the inner wall of the conveying handle;
  when the second key is not pressed, the first elastic component is in a compression state, and the end of the prying section connected to the first elastic component blocks the first control from controlling the core wire to move towards the proximal end of the conveying handle under an anti-compression effect of the first elastic component; and
  when the second key is pressed, the end of the prying section connected to the first elastic component is pried to further compress the first elastic component so as to release the restriction of the second control on the first control to control the movement of the core wire towards the proximal end of the conveying handle.

5. The conveyor for an implant having at least one cavity according to claim 1, wherein the conveying handle is further provided with a second control and a plurality of gears, the maximum distance that the distal end of the core wire is controlled by the first control to pass out of the distal end of the conveying cable is defined when the second control coordinates with the gears.

6. The conveyor for an implant having at least one cavity according to claim 5, wherein for each of the gears, a second protrusion is correspondingly provided on an inner wall of the conveying handle, and the second control comprises a second key, a clamping block and a limiting block, and the clamping block is provided with first grooves cooperating with the second protrusions, and one side, opposite to the first grooves, of the clamping block is provided with a plurality of second grooves, and one side of the limiting block is provided with third protrusions cooperating with the second grooves, and the distal end of the other side of the limiting block is provided with a fourth protrusion, and the clamping block is connected to the limiting block through at least one first elastic component;
  when the second key is not pressed, the second protrusions are clamped with the first grooves; and
  when the second key is pressed until the second protrusions are extracted from the first grooves, the second grooves of the clamping block are clamped with the third protrusions of the limiting block, and the clamping block and the limiting block move along with the movement of the second key.

7. The conveyor for an implant having at least one cavity according to claim 5, wherein the second control comprises a second key and a gear baseboard, and the middle of the second key is fixed on the conveying handle;
  two ends of one side, opposite to the gear baseboard, of the second key are respectively provided with a limiting boss, and one side, opposite to the second key, of the gear baseboard is provided with at least two third grooves, and the second key is connected to the gear baseboard through a limiting member cooperating with the third grooves; and
  the second key limits a distance that the core wire is controlled by the first control to pass out of the distal end of the conveying cable by controlling the matching of the limiting member with different third grooves.

8. The conveyor for an implant having at least one cavity according to claim 7, wherein the limiting member comprises a fixing tube, a first elastic component and a ball, and one end of the fixing tube is fixed on the second key and positioned between the two limiting bosses, and the first elastic component is received in the fixing tube, with one end connected to the second key and the other end connected to the ball; and the first elastic component is in a compressed state, so that the ball is pressed against the third grooves of the gear baseboard and partially received in the fixing tube.

9. The conveyor for an implant having at least one cavity according to claim 7, wherein the limiting member comprises a blind tube and a first elastic component, and the bottom of the blind tube is bulb-shaped, and the first elastic component is partially received in the blind tube, and one end of the first elastic component received in the blind tube is connected to the bottom of the blind tube, and the other end is connected to the first key.

10. A conveyor for an implant having at least one cavity, comprising:
  a conveying handle, a conveying cable and a core wire, the conveying cable being a tubular body, a proximal end of the core wire connected to the conveying handle, and a distal end of the core wire penetrating through a distal end of the conveying cable from a proximal end of the conveying cable, wherein a first control is provided on the conveying handle, and when the implant is connected to the distal end of the conveying cable, the first control controls the distal end of the core wire to extend into the implant to straighten the implant of a preset shape, or the first control controls the core wire to withdraw from the implant to restore the implant to the preset shape;
  the conveying handle is further provided with a second control, wherein the second control comprises a knob, a locking seat and a locking block, the locking seat is an annular body having an opening, the core wire extends through the locking seat, the locking block can extend into the locking seat from the opening, and the knob is an annular body and sleeved outside both the locking seat and the locking block;
  the knob comprises a first rotating area and a second rotating area which are connected, an inner diameter of the first rotating area is larger than an inner diameter of the second rotating area, and when the knob is rotated to make the locking block contact with an inner wall of the second rotating area, the locking block locks the core wire on an inner wall of the locking seat; and
  when the knob is rotated so that one end of the locking block which is far away from the core wire corresponds to an inner wall of the first rotating area, no interaction force exists between the core wire and the locking seat.

11. A conveyor for an implant having at least one cavity, comprising:
  a conveying handle, a conveying cable and a core wire, the conveying cable being a tubular body, a proximal end of the core wire connected to the conveying handle, and a distal end of the core wire penetrating through a distal end of the conveying cable from a proximal end of the conveying cable, wherein a first control is provided on the conveying handle, and when the implant is connected to the distal end of the conveying cable, the first control controls the distal end of the core wire to extend into the implant to straighten the implant of a preset shape, or the first control controls the core wire to withdraw from the implant to restore the implant to the preset shape;

wherein the conveying handle is further provided with a second control, the distal end of the core wire is always closer to the distal end of the implant than the distal end of the conveying cable when the second control is in a locked state and the first control controls the core wire to move within the implant; and when the second control is in an unlocked state and the first control controls the core wire to be completely extracted out from the implant, the implant is released and in the preset shape; and wherein the second control comprises a second key, a prying section and a first elastic component, and one end of the prying section abuts against the second key and the other end is connected to one end of the first elastic component, and the other end of the first elastic component is fixed on an inner wall of the conveying handle, and a prying fulcrum of the prying section is fixed on the inner wall of the conveying handle;

when the second key is not pressed, the first elastic component is in a compression state, and the end of the prying section connected to the first elastic component blocks the first control from controlling the core wire to move towards the proximal end of the conveying handle under an anti-compression effect of the first elastic component; and when the second key is pressed, the end of the prying section connected to the first elastic component is pried to further compress the first elastic component so as to release the restriction of the second control on the first control to control the movement of the core wire towards the proximal end of the conveying handle.

\* \* \* \* \*